United States Patent [19]

Stoy et al.

[11] Patent Number: 5,688,855

[45] Date of Patent: Nov. 18, 1997

[54] THIN FILM HYDROPHILIC COATINGS

[75] Inventors: Vladimir A. Stoy, Princeton; Gerald A. Gontarz, Jr., Helmetta; Patrick Stoy, Princeton, all of N.J.

[73] Assignee: S.K.Y. Polymers, Inc., Rocky Hill, N.J.

[21] Appl. No.: 434,573

[22] Filed: May 1, 1995

[51] Int. Cl.$^6$ .................. C08K 5/15; C08K 5/07; C08K 5/02; C08K 5/06

[52] U.S. Cl. .......... 524/505; 524/113; 524/360; 524/361; 524/323; 524/378; 524/379; 524/462; 524/464

[58] Field of Search .................. 524/113, 360, 524/361, 323, 378, 379, 462, 464, 505

[56] References Cited

U.S. PATENT DOCUMENTS

| | | | |
|---|---|---|---|
| 3,822,238 | 7/1974 | Blair et al. | 528/59 |
| 3,975,350 | 8/1976 | Hudgin et al. | 524/108 |
| 4,026,296 | 5/1977 | Stoy et al. | 604/96 |
| 4,095,877 | 6/1978 | Stoy et al. | 524/505 |
| 4,107,121 | 8/1978 | Stoy | 524/391 |
| 4,156,066 | 5/1979 | Gould | 523/175 |
| 4,156,067 | 5/1979 | Gould | 528/10 |
| 4,183,884 | 1/1980 | Wichterle et al. | 524/167 |
| 4,255,550 | 3/1981 | Gould | 528/59 |
| 4,337,327 | 6/1982 | Stoy | 524/916 |
| 4,359,558 | 11/1982 | Gould et al. | 525/459 |
| 4,379,874 | 4/1983 | Stoy | 524/505 |
| 4,439,583 | 3/1984 | Gould et al. | 525/127 |
| 4,451,635 | 5/1984 | Gould et al. | 528/71 |
| 4,454,309 | 6/1984 | Gould et al. | 525/454 |
| 4,490,423 | 12/1984 | Gould et al. | 525/454 |
| 4,743,673 | 5/1988 | Johnson et al. | 528/60 |
| 4,789,720 | 12/1988 | Teffenhart | 528/76 |
| 4,798,876 | 1/1989 | Gould et al. | 525/457 |
| 4,920,172 | 4/1990 | Daoud | 524/502 |
| 4,921,497 | 5/1990 | Sulc et al. | 427/2.24 |
| 5,120,816 | 6/1992 | Gould et al. | 528/76 |
| 5,217,026 | 6/1993 | Stoy et al. | 524/916 |
| 5,218,039 | 6/1993 | Stoy et al. | 524/566 |
| 5,252,692 | 10/1993 | Lovy et al. | 528/363 |
| 5,278,217 | 1/1994 | Umeda et al. | 524/505 |

*Primary Examiner*—Peter A. Szekely
*Attorney, Agent, or Firm*—Kenneth P. Glynn

[57] ABSTRACT

A hydrophilic coating composition used to impart increased lubricity and wettability to the surface of a hydrophobic substrate which is comprised of three essential components:

1) Hydrogel-forming polymer component A
2) Water-soluble polymer component B
3) Common solvent C for the components A and B The water-insoluble, hydrogel-forming component A consists of a segmented copolymer with long, hydrophilic terminal blocks and the essentially hydrophobic central section. The two polymer components A and B have a limited miscibility in the absence of a common solvent C. Therefore, their blend tends to separate spontaneously into two polymer phases. The phase separation takes place during the solvent evaporation or extraction. A gradient of hydrophilicity and swelling within the coating layer is thus spontaneously created achieving a good adhesion to the substrate and high surface hydrophilicity at the same time.

18 Claims, No Drawings

THIN FILM HYDROPHILIC COATINGS

BACKGROUND OF THE INVENTION:

The hydrophilicity of a solid surface can be an advantage in various situations:

1. Hydrophilic surfaces resist soiling by lipophilic substances such as oils, greases, fuels, spray-paints and waxes.
2. Hydrophilic surfaces often resist the absorption or adhesion of proteins, cells and related biological substances such as incrustations, thrombi or clusters of cells such as platelets.
3. Hydrophilic surfaces often resist fogging; this is an advantage for optical devices such as mirrors, windows, goggles or lenses.
4. Hydrophilic surfaces are often slippery in the presence of water. This can be utilized in bearings, surgical gloves, guide-wires or catheters.
5. Hydrophilic surfaces often show an improved capability to absorb and retain disinfectants, inks or dyes.

These examples suggest a number of practical applications or products benefiting from hydrophilic surfaces: medical devices, surgical gloves, bearings, lenses, mirrors, packaging means, pipes and valves, and many other products.

Most of the materials used for engineering, packaging or biomedical products are generally hydrophobic to various degrees. For instance, many plastics, rubbers and metal alloys are poorly wettable by water. Even glass and ceramics can benefit from a treatment which would render their surface highly wettable, or even swellable in water and/or slippery in the water-wetted state.

There are several methods used to increase the surface hydrophilicity of otherwise hydrophobic materials. For instance, hydrogels are sometimes used to construct an article with improved surface hydrophilicity. This approach has several disadvantages:

First, the swelling of the hydrogel in water, or its deswelling or drying, changes its size, shape and mechanical properties. This may be a considerable complication in a number of instances.

Also, not all hydrogel surfaces are truly hydrophilic or even slippery. It is sometimes necessary to chemically treat the hydrogel articles to introduce ionically charged groups which increase surface hydrophilicity and leave a slippery surface, as it is described in U.S. Pat. No. 4,810,543 by Gould and Kliment, in U.S. Pat. No. 4,183,884 by Wichterle and Stoy, in U.S. Pat. No. 5,217,026 by G. Stoy and V. Stoy or in U.S. Pat. No. 4,026,296 by Stoy, et al. This so called "superhydrophilization" is an additional process step which can considerably complicate the manufacture and use of the final product. It is particularly difficult to create the superhydrophilic surface on very thin hydrogel articles or layers.

Similar methods of surface hydrophilization via chemical treatment can also be applied to some hydrophobic plastics. For instance, the surfaces of poly(acrylamides), poly(methacrylates) and poly(acrylates) can be superhydrophilized by hydrolysis or by reesterification combined with sulfation, as described in U.S. Pat. No. 3,895,169 by Wichterle or in U.S. Pat. No. 4,921,497 by Sulc and Krcova, etc. Plastics containing nitrile groups can be surface-hydrolyzed or aminolyzed as described in the U.S. Pat. No. 4,943,618 by V. Stoy, G. Stoy and Lovy and in U.S. Pat. No. 5,252,692 by Lovy and Stoy.

Hydrophobic polyolefines, such as polyethylene or polypropylene, can be surface-hydrophilized by oxidation, amination or sulfonation by either gaseous or liquid reagents or by other well known methods. The surface is sometimes activated by suitable means such as corona discharge.

Another variant of surface hydrophilization is the grafting of hydrophilic monomers initiated by irradiation or chemical activation of the hydrophobic surface. Such methods are described, for instance, in U.S. Pat. No. 3,826,678, European Patent Application No. 82850200.5, U.S. Pat. No. 4,377,010, U.S. Pat. No. 4,387,183 and U.S. Pat. No. 4,291,133. These surface-modification methods rarely yield a truly hydrophilic, slippery surface. In most cases, it results in increased wettability which, for example, is required for printing and adhesive bonding. Another desired result is improved blood compatibility. These methods are limited to surfaces which are suitably reactive; they can be rarely applied to surfaces such as metals or glass.

Another common hydrophilization method consists in the application of hydrophilic (or hydrogel) coatings. Hydrophilic polyurethanes are often considered the most suitable class of polymers for hydrogel coatings because of their relative flexibility in the dry state, solubility in several kinds of the volatile solvents and reactivity allowing crosslinking or anchoring reactions. Many hydrophilic polyurethanes are described in patent literature (see e.g. U.S. Pat. Nos. 3,822,238; 3,975,350; 4,156,066; 4,156,067; 4,255,550; 4,359,558; 4,920,172; 4,789,720; 4,810,543; 4,743,673; 4,798,876; 4,490,423; 4,454,309; 4,451,635; 4,439,583; 4,255,550), and many of them were suggested as a basis for hydrophilic coatings of catheters and other articles. Another frequently used polymer system is based on poly(2-hydroxyethylmethacrylate), or poly(HEMA). Such coatings are described in, for instance, U.S. Pat. No. 4,527,293; U.S. Pat. No. 3,861,396 and U.S. Pat. No. 3,566,874.

The main problem of the coating approach is that proper adhesion of the coating to the substrate requires a certain similarity between the two (i.e. a certain hydrophobicity). This conflicts with the requirement of the high surface hydration of the coating.

The problem of adhesion increases with the coating hydrophilicity for several reasons:

1. Coatings with high hydrophilicity undergo substantial volume changes during hydration and drying. These changes create stress on the interface which often leads to delamination or peeling.
2. Highly hydrophilic coatings are primarily composed of polymers with highly polar groups which are hydrated in the presence of water. While hydrated, these groups cannot enhance the adhesion between the surfaces.
3. The large difference in wetting characteristics implies a large difference in the cohesion energies of both materials, and thus a high interfacial free energy in the bonded state. Such a configuration poses a basic thermodynamical instability.
4. Highly hydrophilic polymers are often rigid or even brittle in the dry state. Their rigidity leads to cracking, peeling and flaking off the substrate.

This inherent problem can be solved by a combination of several methods of various technical complexity. The methods most frequently used are the following ones:

1. The hydrophilic layer can be "anchored" to the substrate by chemical bonds reaching across the interface. This bonding has to be carried out in such a way that it does not affect the surface hydrophilicity. Such reactive hydrophilic coatings are described in European Patent No. 00993093B1 and British Patent No. 1,600,963. Micklus et al. therein describe hydrophilic coatings comprised of a water-soluble polymer (polyvinylpyrrolidone) and a pre-polymeric component with reactive isocyanate groups which inter-crosslinks the soluble polymer and anchors it to the surface of the substrate. Another hydrophilic coating in which a hydrophilic polymer is covalently bonded to a hydrophobic surface is described by Terumo Corporation it its European Patent No. 0166998B1. Such reactive coatings have many disadvantages. The crosslinking and anchoring reactions have to be carefully controlled to achieve the desired results. If the coating conditions are not exactly right, the whole product can be destroyed. Moreover, the coating compositions are unstable, and the reactive components are usually toxic.

2. The transition between the hydrophilic coating and the hydrophobic substrate is created in such a way that the hydrophilicity increases gradually from the substrate to the surface. This can be achieved e.g. by applying several layers of coatings of increasing hydrophilicity. This method is laborious and the application of successive coating layers is often difficult without dissolving the layers underneath. The control of the coating thickness and control of the gradient of hydrophilicity are generally difficult.

Another method of creating the swelling gradient comprises of a controlled penetration of hydrophilic monomers into a hydrophobic substrate. The penetration is often supported by the use of solvents. Once the monomers are diffused into the surface, they are polymerized within the substrate structure which creates the gradient and at the same time anchors the hydrophilic layer, as described, for instance, in the U.S. Pat. No. 3,961,379. Since the gradient depends on the rate of the monomer penetration, the control of this process is usually rather difficult and not very reliable.

Still another method is the creation of a substantially hydrophobic coating which adheres well to the substrate in one step, and then surface-modifying the coating by a suitable method to render it more hydrophilic. For instance, polyurethane coatings are sometimes treated with acids to render their surface hydrophilic and more lubricious e.g., see the U.S. Pat. No. 4,810,543). The surface treatment must not reach the interface with the substrate lest the adhesion could be lost. This is an obvious problem for very thin coatings.

3. The hydrophilic coating is often plasticized to soften the layer in the dehydrated state and to alleviate some of the adhesion problems. However, the plasticizers of the hydrophilic polymers are mostly water-soluble so that this is usually only a temporary measure.

The coatings are applied by various methods including dipping and spraying of polymer solutions, such as in U.S. Pat. No. 4,589,873, and/or the reactive liquid precursors. Such coatings are often based on hydrophilic polyurethanes, such as those described in U.S. Pat. No. 5,120,816 by Gould, et al. and in U.S. Pat. No. 4,920,172 by S. Daoud. The coatings described therein also suffer from the above mentioned shortcomings and do require complicated processes involving chemical cross-linking and post-treatment surface hydrophilization reactions.

SUMMARY OF THE INVENTION

According to the invention, the hydrophilic coating composition is comprised of three essential components:
1. Hydrogel-forming polymer component A
2. Water-soluble polymer component B
3. Common solvent C for the components A and B The water-insoluble, hydrogel-forming component A consists of a segmented copolymer with long, hydrophilic terminal blocks and the essentially hydrophobic central section. The component A can be described by the general formula

$$T_1-X-T_2$$

where $T_1$, $T_2$ are the hydrophilic terminal blocks and X is the hydrophobic central section comprising one or more hydrophobic blocks or sequences. (By "hydrophobic blocks" it is meant sequences of monomer units such that a polymer of the same length and composition would be neither soluble nor substantially swellable in water. By "hydrophilic blocks" it is meant sequences of monomer units such that a polymer of the same length and composition would be soluble in water.)

The two polymer components A and B have a limited miscibility in the absence of a common solvent C. Therefore, their blend tends to separate spontaneously into two polymer phases. The hydrophobic blocks or sequences of the component A tend to separate and accumulate at the interface with the hydrophobic substrate, while the water-soluble component B tends to accumulate at the surface of the coating. The separation of the component B also supports the separation of the hydrophilic terminal blocks T of the component A. The phase separation takes place during the solvent evaporation or extraction. A gradient of hydrophilicity and swelling within the coating layer is thus spontaneously created achieving a good adhesion to the substrate and high surface hydrophilicity at the same time.

DETAILED DESCRIPTION OF THE INVENTION

The polymer component A is insoluble in water, but it dwells in contact with water forming a hydrogel. The typical water content in such a hydrogel at equilibrium is between about 50% and 99% by weight, preferably between 75% and 95% by weight.

The terminal blocks of the component A, $T_1$, $T_2$, can be chemically identical or dissimilar. At least one of them has to have a high hydrophilicity and a sufficient length to separate from the hydrophobic central section during the drying. From the chemical viewpoint, the terminal blocks can be based on polymers and copolymers of acrylic acid; methacrylic acid; hydrophilic esters of acrylic and methacrylic acid, such as esters of polyglycols, glycerol or sugars; alkylene oxide; maleic acid; styrenesulfonic acid; vinylpyrrolidone; acrylamide and N-substituted acrylamide; or methylvinylether. They can be also based on water-soluble polysaccharides, such as dextranes, dextrane sulfate, carboxymethylcellulose, chondroitin sulphate or hyaluronic acid.

Particularly important for medical products are terminal blocks comprising polyether chains which are strongly hydrophilic while lacking the proton-donor capability and which are known to be resistant to protein adsorption.

The average length of the terminal blocks $T_1$ and/or $T_2$ is typically more than about 25 monomer units, and preferably more than about 100 monomer units, to guarantee the necessary phase separation. It is understood that the terminal blocks in a coating composition can be of different lengths and of different composition. It is possible, for instance, that some molecules of the component A have only one terminal block of the said characteristics, or that there are several types of terminal blocks present in one component A.

The central section X of the component A is a water-insoluble polymer chain comprising of one or more substantially hydrophobic polymer blocks or sequences. The section X can be described by the formula $$-(HB-L)_n-HB-$$

where HB is the hydrophobic (or "hard") block and L is the linking sequence. The subscript $\underline{n}$ can be between 0 and about 15, preferably between 1 and 10.

The blocks HB can be based on various known hydrophobic (or water-insoluble) polymers. For instance, they can be based on polymers with carbon-carbon backbone, such as polymers and copolymers of esters, N-alkylacrylamides and nitriles of acrylic and methacrylic acids; styrene; vinylacetate; vinylformal or vinylbutyral.

The blocks HB can be also based on polymers with an hetero-atoms in their backbones. Example of these polymers are polyamides, such as condensates of adipic acid and 1,6-hexamethylene diamine; polyesters, such as glycol esters of terephthalic acid; polyepoxides; aliphatic, cycloaliphatic or aromatic polyurethanes and polyureas; polyphosphazenes; and polysiloxanes.

Unless stated otherwise, all molecular weight averages in our application are number averages.

The average molecular weight of the individual block HB can vary in a broad range, typically between about 500 and about 50,000 Daltons; preferably between about 1000 and 20,000 Daltons. All molecular weights herein are number average molecular weights, unless otherwise specified. Hard block capable of forming crystalline clusters, such as sequences with pendent nitrile groups in 1,3 (i.e. alternating) positions can be of a substantially lower molecular weight, starting from about 250 Daltons. Also compositions with a multitude of the hard blocks can perform well even though the individual block length is relatively small. The compositions with several shorter HB blocks are generally preferred over those with one very long central HB block.

The linking sequence L can be either hydrophobic or hydrophilic, of average molecular weight generally not exceeding about 25,000 Daltons. The linking sequence L is preferably derived from various diols such as ethylene glycol, diethylene glycol, triethyleneglycol, 1,2- or 1,3-propanediol, 1,3- or 1,4-butanediol, polyethylene oxide, polypropylene oxide and the like. They can be also derived from diamines, such as hexamethylene diamine, or an ($\alpha,\omega$-)diamino-terminated poly(ethylene oxide). The linking sequences L can be also formed by blocks comprising derivatives of acrylic or methacrylic acids or vinylalcohol. It is understood that the linking sequences L present in one molecule of component A or in one coating formulation can be of different length and of different chemical composition. It is possible, for instance, that some molecules of component A have no linking sequence L, while others have several types of linking sequences L present in one coating formulation.

Component A can be a block copolymer with one hydrophobic block and with one or two hydrophilic terminal blocks. There are many synthetic methods for the block copolymers well known to those skilled in the art.

One class of the block copolymers useful as the component A are multiblock copolymers formed by reactions of a precursor polymer with hydrophobic pendent groups, such as polyacrylonitrile or polyvinylacetate. Such polymer reactions (e.g., hydrolysis) can yield multiblock copolymers with hydrophobic and hydrophilic sequences by the so called "zipper mechanism". If the reaction conditions are correctly selected, the hydrophilic sequences form one or both terminal sequences $T_1$, $T_2$ while the hard blocks HB are sequences with the original hydrophilic pendent groups. The linking sequences L are formed by hydrophilic blocks of the same character as the terminal sequences $T_1$ and $T_2$.

The multiblock copolymers of this kind are described in several patents, such as in U.S. Pat. Nos. 5,252,692; 4,943,618; 4,107,121; 4,337,327; 4,379,874; 4,420,589; 3,897,589. The copolymers described in these patents are well known for their phase separation which is an important feature for the present inventions. Copolymers which are particularly useful for the present invention are described as the polymeric emulsifiers in the U.S. Pat. No. 5,218,039 and are thereby included by this reference.

The block copolymers with the central section X comprising one or more HB blocks derived from polyurethane, polyurea or polyurea-polyurethane copolymers are particularly suitable for the coatings according to our invention. They have several advantages:

1. There is a broad selection of solvents for this type of copolymers, including readily volatile solvents and solvents dissolving also various water-soluble polymers.

2. The copolymers of this type are relatively flexible even in the dry state; therefore, there is no need for plasticizers.

3. The copolymers of this type can be readily synthesized by well known methods from commercially available reactive precursors The copolymers of this preferred type have the hard block HB of the general formula $$(-CO-NH-R_1-NH-CO-NH-R-NH)_a-CO-NH-R_1NH-CO-(O-R3-O-CO-NH-R4-NH-CO-)_b$$

where a has a value between 0 and 15, preferably between 2 and 10; b has a value between 0 and 10, and preferably between 1 and 5; and where $R_1$, $R_2$ and $R_4$ are the same or mutually different aliphatic, cycloaliphatic or aromatic substituents; and where $R_3$ is an aliphatic, cycloaliphatic or aromatic substituent or an ether of the formula $$-CH_2-CH_2(-O-CH_2-CHZ)_i-$$

where $\underline{i}$ is an integer 1 to 3 and $\underline{Z}$ is a substituent selected from the group consisting of hydrogen, an alkyl, and a halogen.

One of the particularly preferred HB structures is a polyurea block formed by the reaction between methylene-bis-cyclohexyldiamine and methylene-bis-cyclohexyl-diisocyanate (DESMODUR W, Mobay Corp.)

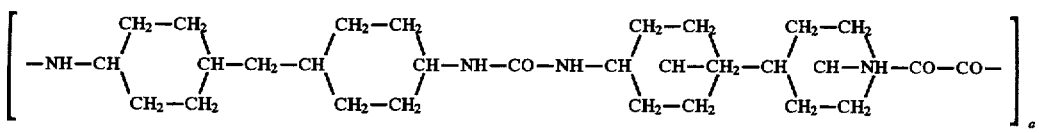

where the average a is between 1 and 15 and preferably between 2 and 10. The blocks with a>15 are difficult to dissolve in solvents compatible with the other requirements.

The polyurea blocks can be interconnected via shorter or longer polyether chains by urethane links, such as in

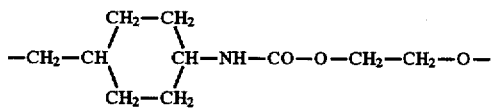

The connecting polyether chains can be derived from various diols such as ethylene glycol, diethylene glycol, triethyleneglycol, 1,2- or 1,3-propanediol, 1,3- or 1,4-butandiol, polyethylene oxide or polypropylene oxide up to a molecular weight of about 500 Daltons, and the like.

Component A has to be soluble in certain solvents and capable of a phase separation of its segments with different polarity. Therefore, k must not be covalently crosslinked or even extensively branched.

Solvents dissolving the component A have to solvate both the hydrophobic central section X and the hydrophilic terminal blocks T. For that reason it is often advantageous to use a mixture of solvents of different polarity.

Component B is comprised of a water-soluble polymer which is at least partly incompatible with component A so that is has only a limited blending capability with the component A in absence of a common solvent. Component B is also soluble in some of the solvent capable of dissolving component A.

Component B comprises various hydrophilic functional groups, such as ethers (e.g. in a polyethylene oxide, in poly(methylvinyl ether) or in a block copolymer polyethyleneglycol-polypropyleneglycol); carboxyls (e.g., in polyacrylic acid or in copolymers of maleic acid), hydroxyls (e.g. in polyvinylalcohol or in carboxymethyl cellulose), amides (e.g. in polyacrylamide, poly(N-isopropyl acrylamide) or in polyvinylpyrrolidone), sulfonic acid (e.g., in polyvinylsulfonic acid or polystyrene sulfonic acid), sulphate (e.g., in dextran sulphate or chondroitin sulphate).

The length of the polymer chain of the component B is an important consideration. Component B should have at least 100 monomer units, preferably more than 200 monomer units to achieve at least moderate incompatibility with the component A. The upper limit of the polymer chain length is given by the requirements of solubility and compatibility with component A in a common solvent. Depending on the chemical composition of both components A and B, this upper limit is typically between 1000 and 20,000 monomer units.

The ratio between the components A and B has to be in a certain range to achieve the correct phase separation. Thus, A:B is generally between 3:1 and 1:3, and preferably between 3:2 and 2:3 by weight.

The common solvent component C has to be capable of dissolving both polymer components A and B. Examples of usable solvents are alcohols C1–C6, such as methyl-, ethyl, isopropyl-, n-butyl, iso-butyl, t-butyl or cyclohexyl alcohols; phenols; ketones, such as acetone or methylethyl ketone; ethers, such as dioxane or tetrahydrofurane; chlorinated hydrocarbons such as methylene chloride, chloroform or tetrachloroethylene; aromatic hydrocarbons, such as benzene, toluene, chlorobenzene or xylene; or dipolar solvents such as DMSO, tetramethylene sulfone, DMF or gamma-butyrolactone; concentrated or partially diluted acids such as acetic acid; formic acid; phosphoric acid; nitric acid; and aqueous solutions of certain salts, such as zinc chloride; sodium thiocyanate; magnesium perchlorate; and lithium bromide.

Because the formulation contains polymeric components of different polarity, it is often advantageous to use mixtures of two or more solvents. It is also often advantageous to use mixtures of the said solvents with water which improves solvatation of highly polar moieties of components A and B. Its concentration is limited by the necessity to avoid precipitation the less polar moieties of the component A. As a rule and depending on the components A and B, water can be present in organic solvents in concentrations between about 0.25 and 15%, and more typically between about 1% and 10% by weight to have the desirable effect on the solvent dissolution capability. In inorganic acids and salts, water concentration can be as high as 50% by weight.

The concentration of the components A and B can vary in a broad rage, between about 0.25% and 10% by weight, depending on the molecular weight of the components, on the desired thickness of the coating, and on other circumstances. Low concentrations are preferred for several reasons:

a) Improved miscibility of components A and B in the solution b) Formation of very thin coatings c) More efficient phase separation during drying The typical useful concentration of the solids in the coating ranges between about 1% and 5% by weight. Diluted solutions can be used for very thin coatings, thinner than 0.1 mm or even below 0.01 mm.

The phase separation of the polymeric components A and B, which is necessary for the coating's adhesion, is achieved simply by evaporation of the common solvent C. We have found that the thinner the layer, the more efficient the phase separation and better the final coating properties. It appears that the separation in thicker layers takes place in a different manner than in very thin layers. While hydrophobic moieties in the thick layers separate into clusters forming a physically crosslinked hydrogel, the same composition in a thickness below about 25 microns appears to form a layered phase-separated structure. Consequently, the coatings of a very small thickness has markedly improved adhesion and also, at the same time, an improved wet friction. This is a surprising finding because other types of coating show, as a rule, the opposite trend (i.e., the lubricity improves with the increasing thickness of the coating). The improvement of the properties is particularly obvious if its thickness is decreased to several microns or even less.

The phase separation of the hydrophilic and hydrophobic polymer moieties can be further supported by selection of solvents of various volatility and polarity. Another helpful factor is the absorption of water from a humid environment into the drying layer. The moisture absorption creates a gradient of water concentration which supports the phase separation and formation of the hydrophilicity gradient within the coating. For that reason, it is advantageous to select water-miscible solvent(s) and carry out the evaporation at a relatively low temperature (such as a room temperature) and at relative humidity of at least 50% and preferably at a humidity higher than 75%. It is also sometimes possible to achieve the phase separation by exposing the coating composition layer to steam, water mist or spray of water droplets. Sometimes we can even dip the coated article into water to achieve the phase separation by coagulating component A and replacing the component C for water.

Water can also be added to the solvent system to promote the phase separation. Even 0.5% to 15% percent water in the solvent can support the phase separation once the polymer concentration increases due to the solvent evaporation. Preferred range of the water concentration is 5% to 10% by weight. It is also advantageous to use water-miscible liquids as a part of the solvent system which has a boiling point below that of water, and especially below about 85° C.

The water-soluble component B serves primarily to promote the phase separation and orientation of the hydrophilic moieties of the component A. At least part of the component B is physically entrapped in the coating and contributes to its hydrophilicity. This effect can be enhanced by moderate inter-crosslinking of the components A and B after the phase separation has been completed. This can be achieved in various ways.

The most convenient crosslinking method involves irradiating the dry or semi-dry coating with ionizing radiation, including gamma-radiation, X-rays, Beta-radiation or electron beam radiation. As a rule, the irradiation dose should range from about 0.25 to about 10 MRad, but usually a dose between about 1 and 5 MRad will be sufficient. The radiation crosslinking can be advantageously combined with sterilization. The radiation dose and/or the radiation energy can be decreased by the use of photoinitiators or sensitizers, such as benzoin, and/or reactive groups, such as cinnamyl or pendant vinyl groups, or reactive plasticizers, such as suitably selected monomers. In this case, even UV radiation can be used for crosslinking and stabilization of the coating.

The coating can also be thermally crosslinked by various reactions, such as etherification, reesterification or transamidation. The crosslinking can be facilitated by introduction of suitable reactive groups, such as "masked isocyanates" (e.g., adducts of isocyanate to caprolactam or phenol).

There are numerous crosslinking techniques known to those skilled in the art which can be adapted to our invention. The main point in their application is to postpone the crosslinking until only after the phase separation of the hydrophilic and hydrophobic moieties has been achieved.

The coating compositions according to our invention can be readily applied to a substrate by dipping, spraying, and the like. The substrate should be thoroughly cleaned to remove surface impurities which could interfere with adhesion. It is recommended that various plastic or polymeric substrates be treated with oxidizing solutions prior to the coating application. For instance, natural rubber can be treated with a sodium chlorate solution; other polymers can be treated with diluted potassium permanganate solution, and the like.

The hydrophilic coatings according to our invention can be made to adhere well to a number of materials:

synthetic and natural rubbers; polyolefines, such as polyethylene, polypropylene or polymethylpentene; vinylic polymers, such as polyvinylchloride or polyvinylidene fluoride; polystyrene and its derivatives and copolymers, such as SAN or ABS plastics; polysiloxanes; polyurethanes and polyureas; polyacrylates, such as polyacrylonitrile, polyethylacrylate, and the like; polymethacrylates, such as polymethylmethacrylate, polyalkylmethacrylates, polymethacrylonitrile and various copolymers thereof, polycarbonates; polyphosphazenes; cellulose and its derivatives; glass; ceramics; metals and alloys, such as stainless steel, alloys of titanium, aluminum, nickel, copper and other metallic materials; wood; laminates; cotton; and many other natural or synthetic materials.

The versatility of substrates and easy application makes the coatings suitable for many product areas. Some examples:

Medical devices, such as catheters, guidewires, cystoscopes, stents, hypodermic needles, biopsy needles, forceps, sutures, gastric tubes, laparoscopy devices and many others.

Coatings protecting masonry, laminates or painted surfaces against graffiti or dirt and facilitating their cleaning.

Anti-fogging coatings for windows, mirrors, lenses, goggles, visors, displays and similar optical elements.

Protective coatings on textile, aprons or gloves preventing the adhesion of glues, oils, greases or precursors of resins.

Coatings improving the wetting of the internal surfaces of heat- or mass exchangers, such as scrubbers, gas absorbers or evaporative coolers which can benefit from the stability of a thin aqueous film.

Coatings on fishing lures, water slides or chutes, valves, propellers or impellers, beatings and other surfaces benefiting from low wet friction, low adhesion of lipophilic substances and improved wetting.

The components of the coatings according to our invention may be either commercially available polymers, or compounds specifically synthesized for this task. The component A may be synthesized by numerous techniques usual in polymer chemistry which are well known to those skilled in the art.

One preferred synthetic route for the component A comprises a synthesis of a precursor of the hydrophobic central block X equipped with the reactive end-groups, such as hydroxyls; carboxyls; acylhalides; epoxy groups; amino groups; or isocyanate groups and their adducts with phenols, caprolactam or similar masking groups.

The hydrophobic precursor with the reactive ends can then be reacted with monomers or precursors of the hydrophilic terminal sequences $T_1$ and/or $T_2$, each of which is equipped with one or more groups capable of reacting with the end groups of the precursor X. The following are some examples:

1) Hydrophobic epoxy-terminated prepolymer is reacted with a hydrophilic amino-compound:

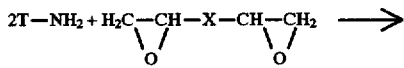

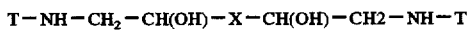

2) Carboxyl-terminated hydrophobic prepolymer is reacted with ethylene oxide:

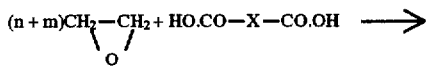

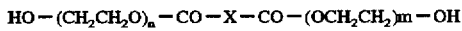

3) Hydroxyl-terminated hydrophobic prepolymer is activated by $Ce^{4+}$ to form terminal free radicals initiating polymerization of acrylonitrile. In the next step, the terminal polyacrylonitrile sequences are hydrolyzed by an alkali to form a hydrophilic acrylate copolymer:

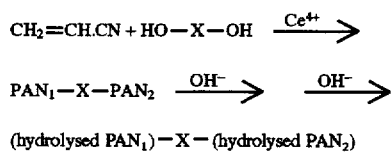

4) Isocyanate-terminated prepolymer is reacted with a hydrophilic hydroxyl-terminated polymeric compound:

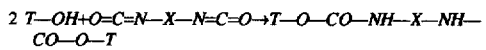

The coatings according to our invention can be combined with various additives, such as disinfectants, surfactants, dyes, pigments, radioopaque fillers, coagulants, drugs, antibiotics, biocides or other biologically active substances. Because of the absence of reactive components and mild application conditions, our coating compositions are particularly suitable as carriers of sensitive biological materials, such as hormones, enzymes, proteins, growth factors, cell proliferation promotors and inhibitors.

Our invention is illustrated by the following non-limiting Examples:

EXAMPLE 1

Hydroxyl-terminated poly(isobutylene) having a molecular weight of 10,000 Daltons is dissolved in hot tetrahydrofurane (THF). A small amount of metallic sodium is dissolved as the catalyst, and ethylene oxide is fed into the reaction mixture under pressure. The progress of the ethoxylation reaction is followed by the pressure decrease caused by the ethylene oxide consumption. The poly(ethylene glycol)- terminated block copolymer is isolated by evaporation of the solvent followed by extraction of the product with water. The product is insoluble in water but swells in water considerably. The calculation indicates that the average molecular weight of the terminal blocks is between 8,000 and 12,000 Daltons.

10 parts by weight of the purified component A is dissolved in THF and 5 weight parts of the poly (vinylpyrrolidone) of average molecular weight 30,000 Daltons is added as the component B. The composition can be used to form a thin lubricious protective coating on various surfaces, such as mansory, plastics, laminates or leather. The protected surfaces are readily cleanable with water in order to remove graffiti or dirt.

EXAMPLE 2

Polyacrylonitrile (PAN) of average molecular weight 175,000 Daltons is dissolved in 65% nitric acid and hydrolyzed at 20° C. for 200 hours as described in the Example 2. of the U.S. Pat. No. 3,948,870. The copolymer can be coagulated from its reaction mixture by water. The product is a hydrogel-forming multiblock copolymer of 10% molar acrylonitrile, 2.5% molar acrylic acid and 87.5% molar of acrylamide with prevailing acrylamide terminal sequences. 15 grams of this copolymer is dissolved in 950 grams of DMSO. Evaporation of the DMSO leaves a polymer layer which can be hydrated with water to form a hydrogel with about 78% of water. The layer in this form is neither well wettable with water nor particularly slippery after hydration. The formulation of the coating solution was finished by adding the component B, namely, 10 grams of polyacrylic acid of molecular weight 50,000 Daltons. The final solution is used to impregnate poly(tetrafluoroethylene) microfiltration membrane. The impregnated membrane is exposed first 100% humidity for several hours, then washed briefly in water and finally dried at 125° C. A stable hydrophilic polymeric film is formed on the hydrophobic fluoropolymer surface. The filter is readily wettable with water without changing its filtration characteristics.

EXAMPLE 3

The hydrophilic segmented polyurethane containing urethane and urea bonds is prepared in the following manner:

0.4 moles of hexamethylene diamine is slowly added to a solution of 1 mol of toluyldiisocyanate (a mixture of 80% of 1,4- isomer and 20% of 2,6 isomer) in tetrahydrofuran (THF). The reaction is completed in about 1 hour under reflux and stirring. The reaction mixture thus obtained is admixed into the molten mixture comprising of 0.1 mol of ethylene glycol, 0.45 mol of polyethylene glycol with average molecular weight 15,000 Daltons, 0.1 mol of polyethylene glycol with average molecular weight 100,000 Daltons and 0.02 mol of triethanolamine.

This mixture is stirred under reflux for 6 hours, then cooled down and diluted with methyl alcohol to a solids content of 5% by weight. Three (3) parts by weight of this solution is mixed with 2 parts by weight of 5% solution of poly(vinylmethyl ether) in toluene and heated while stirring until a homogeneous composition is obtained. The resulting translucent solution is used for the impregnation of protective apparel and footwear to improve its cleanability and resistance against oil and lipophilic toxic substances. The coating is insoluble in hot water, but swells in water to form a lubricious surface which is resistant to soiling by oily substances.

EXAMPLE 4

1.69 mol of (methylene bis(cyclohexyl-4-amine) is reacted with 2.93 mol of (metylene bis(cyclohexyl-4-isocyanate) to form a polyurea prepolymer of molecular weight of about 3,200 Daltons which is terminated with isocyanate groups.

This precursor is added to a molten mixture of 1.06 mol of polyethylene glycol of an average molecular weight of 8,000 D; 2.25 mol of dietylene glycol, and 0.001 mol of dibutyl dilauryl tin. The hot reaction mixture is poured onto a conveyer belt passing through an oven. The reaction mixture passes through the hot zone at about 105° C. in the course of about 30 minutes. The reaction is substantially completed during this pass.

The resulting composition consists of about 45% of the component A which is a segmented polyurethane copolymer with polyoxyethyene terminal sequences and a polyurethane-polyurea central section; and of about 55% of the component B which is the diethylene glycol—polyethylene glycol mixture.

The composition is insoluble in water. In contact with water, the polymer forms a hydrogel containing about 85% water in equilibrium. The polymer mixture is soluble in various organic solvents, including ethyl alcohol, mixture of ethanol-tetrahydrofurane and ethanol-water 9:1 by weight.

These solutions can be used directly to form hydrophilic coatings adherent on various plastics and metals.

EXAMPLE 5

3.4 mol of 1,6-hexamethylenediamine is mixed with 6 mol of 1,5-naphtylenediisocyanate, 4 mol of ethylene glycol, 1 mol of poly(ethylene glycol) of the average molecular weight 5,000 Daltons, 1 mol of poly(ethylene glycol) of the average molecular weight 15,000 Daltons and 0.003 mol of dibutyl dilauryl tin. The reaction mixture is heated to 100° C. for about 2 hours, and then it is transferred to an excess of cold water. The swelled pellets of tie hydrogel-forming segmented polyurethane are extracted in cold water for 2 days to remove the water-soluble components. The polymer component A is then dried and ground to a coarse powder.

3 grams of the component A is dissolved in 97 grams of 1:1 by weight mixture of THF and toluene. 0.4 grams of poly(methylvinylether) of molecular weight 100,000 Daltons is added. The solution is used to coat rubber to achieve a hydrophilic surface which is very slippery and lubricious in cold water but adhesive at an elevated temperature. This property is useful, for instance, for skin adhesives.

EXAMPLE 6

Foley catheter made from natural rubber is dipped into 3% solution of the polymeric composition from the Example 4 dissolved in the ethanol (containing 4% of water)-THF 9:1 by weight. The solution is dried at 20° C. and 80% relative humidity.

Once the surface film loses its tackiness, the drying is finished in an oven at 75° C. The resulting glossy surface layer is less than 0.1 mm thick. It is firmly adherent to the rubber surface both in the dry and wet state. Even the dry layer is sufficiently flexible to withstand the catheter flexing and inflation of the rubber balloon without cracking or flaking off.

The surface layer hydrates quickly and becomes slippery within several seconds after immersion in water. The lubricious layer maintains its properties even after a prolonged (30 days) immersion in isotonic saline at 37° C.

EXAMPLE 7

20 grams of the polymer composition from the Example 4 is dissolved in 900 grams of ethanol to form a clear solution. 80 grams of water is added to this solution while stirring. The liquid becomes cloudy during the water addition.

The resulting liquid is used for coating of metal surfaces, such as stainless-steel hypodermic needles and guidewires made from a Nickel-Titanium alloy.

The very thin layer (below approx. 5 microns) thus formed is firmly adherent to the substrate both in dry and wet state. The wet friction of the surface is considerably decreased due to the coating.

EXAMPLE 8

The guidewire with the hydrophilic coating from the Example 7 is sterilized by electron beam of energy 4 MeV at various radiation doses from about 0.5 MRad to about 15 MRad.

The dry and wet adhesion and the wet friction of the coated guidewires is tested prior and after irradiation. The samples irradiated by doses above about 0.75 MP, ad show improved wet friction, with optimum result between about 1.5 and 5 MRad. The coatings irradiated by more than about 10 MRad are damaged and their adhesion to the substrate is decreased.

EXAMPLE 9

The Foley catheter from Example 6 is sterilized by gamma irradiation from $^{60}$Co source at the dose of 2.7 MRad. This irradiation improved the catheter wet lubricity without any detectable degradation of other properties (adhesion, flexibility, color etc.).

EXAMPLE 10

1 gram of azoadamantane and 0.5 grams of benzalconium chloride is admixed into 1000 grams of the dipping solution from the Example 7. The solution is then sprayed onto glass or ceramic surfaces such as mirrors, windows and wall tiles. The hydrophilic coating thus formed is thinner than 1 micron in dry state and adherent to the surface in both wet and dry state. The surfaces with the hydrophilic coating have improved resistance against fogging and mildew accumulation as well as improved cleanability.

We claim:

1. A hydrophilic coating composition for hydrophobic substrates, comprising:

A mixture of a hydrogel-forming polymeric component A and a polymeric water-soluble component B in a common solvent C, wherein the said polymer component A is capable of forming a hydrogel containing 50% to 99% water in equilibrium, and wherein the said component A is a segmented copolymer of a general formula $$T_1-X-T_2$$

wherein $T_1$, $T_2$ are terminal hydrophilic segments and the central section X comprises at least one hydrophobic polymer sequence.

2. A hydrophilic coating composition for hydrophobic substrate according to claim 1 wherein at least one of the said terminal sequence $T_1$ and/or $T_2$ is a hydrophilic sequence comprising at least 25 hydrophilic monomer units selected from the group consisting of acrylic acid, methacrylic acid, hydrophilic esters of acrylic or methacrylic acid, hydrophilic amides of acrylic or methacrylic acids, alkylene oxide, ethylene oxide, maleic acid, styrenesulfonic acid, vinylsulfonic acid, vinylpyrrolidone, methylvinylether and saccharide units.

3. A hydrophilic coating composition for hydrophobic substrates according to claim 1 wherein the said central section X of the component A is a water-insoluble polymer chain described by the formula $$-(HB-L)_n-HB-$$

where HB is a substantially hydrophobic sequence block and L is the linking sequence, whereas n is a number between 0 and 15.

4. A hydrophilic coating composition for hydrophobic substrates according to claim 1 wherein the said polymeric components A and B are present in a weight ratio between 9:1 and 1:3.

5. A hydrophilic coating composition for hydrophobic substrates according to claim 3 wherein the said hydrophobic blocks HB are polymers and copolymers selected from the group consisting of polymers of esters, N-alkylacrylamides, nitriles of acrylic acid, nitriles of methacrylic acid, styrene, methyl styrene, vinyl acetate, vinyl formal, and vinylbutyral, and polyamides, polyesters, polyepoxides, aliphatic polyurethanes, cycloaliphatic polyurethanes, aromatic polyurethanes, aliphatic polyureas, cycloaliphatic polyureas and aromatic polyureas.

6. A hydrophilic coating composition for hydrophobic substrates according to claim 1 wherein the number average of molecular weight of the individual block HB is between about 250 and about 50,000 Daltons.

7. A hydrophilic coating composition for hydrophobic substrates according to claim 3 wherein the linking sequences L are either hydrophobic or hydrophilic chemical moieties having a number average of molecular weight lower than 25,000 Daltons.

8. A hydrophilic coating composition for hydrophobic substrates according to claim 3 wherein the said linking sequences L are chemical moieties having radicals selected from the group consisting of ester, ether, amide, urethane, urea, imide and imine radicals.

9. A hydrophilic coating composition for hydrophobic substrates according to claim 5 wherein the said hydrophobic segments HB are of the general formula

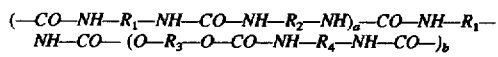

where $\underline{a}$ is a number between 1 and 15, $\underline{b}$ is a number between 0 and 10, where $R_1$, $R_2$ and $R_4$ are the same or different aliphatic, cycloaliphatic or aromatic hydrocarbon substituents; and where $R_3$ is an aliphatic substituent of ether having the formula

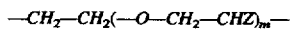

where $\underline{m}$ is a number between 0 and 3 and Z is a substituent selected from the group consisting of hydrogen; alkyl with 1 to 4 carbons; a halogen; and —$CH_2$—COOH.

10. A hydrophilic coating composition for hydrophobic substrates according to claim 9 wherein at least one of the said substituents $R_1$, $R_2$ and $R_4$ are of the formula

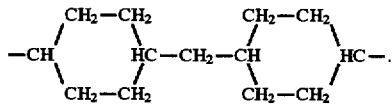

11. A hydrophilic coating composition for hydrophobic substrates according to claim 1 wherein said component B comprises a water-soluble polymer having polar radicals selected from the group consisting of hydroxyl, ether, carboxyl, amine, imine, amide, lactam, lactone, amidine, quaternary ammonium salt, sulfonic acid and sulphate radicals.

12. A hydrophilic coating composition for hydrophobic substrates according to claim 1 wherein the said water-soluble component B comprises a polymer selected from the group consisting of polyalkylene oxide, poly(vinylpyrrolidone), poly(vinyl methyl ether), poly(N-alkylacrylamides), poly(methacrylamide), poly(acrylic acid), poly(methacrylic acid), poly(ethyleneglycol), copolymers of poly(ethyleneoxide-propyleneoxide), poly(ethyleneoxide), copolymers of maleic acid, poly(vinylalcohol), poly(ethyleneimine), carboxymethylcellulose, polyvinylsulfonic acid, polystyrene sulfonic acid, hyaluronic acid, heparin, dextran, dextran sulphate and chondroitin sulphate.

13. A hydrophilic coating composition for hydrophobic substrates according to claim 1 wherein the said water-soluble component B comprises a water-soluble polymer composed from 100 to 20,000 monomer units.

14. A hydrophilic coating composition for hydrophobic substrates according to claim 1 wherein the said common solvent component C comprises a liquid selected from the group consisting of tetrahydrofuran, dioxane, dialkylether, acetone, methylethylketone, lower halogenated hydrocarbons C1–C6, lower aliphatic alcohols C1–C6, benzene, toluene, xylene, cyclohexanone, acetonitrile, alkylacetate, tetramethylene sulfone, dimethylsulfoxide, g-butyrolactone, phenols, formic acid and acetic acid.

15. A hydrophilic coating composition for hydrophobic substrates according to claim 1 wherein the said common solvent comprises between 0.25% and 15% of water.

16. A hydrophilic coating composition for hydrophobic substrates according to claim 1 wherein the said common solvent component C is an aqueous solution of a substance selected from the group consisting of sodium thiocyanate, potassium thiocyanate, calcium thiocyanate, zinc chloride, lithium bromide, magnesium perchlorate, phosphoric acid, nitric acid and sulfuric acid.

17. A hydrophilic coating composition for hydrophobic substrates according to claim 1 wherein the said common solvent component C constitutes more than 95% by weight.

18. A hydrophilic coating composition for hydrophobic substrates according to claim 1 comprising in addition to the components A, B and C also another component selected from the group consisting of a surfactant, a pigment, a dyestuff, an antibiotic, a disinfectant, a bactericide, a biocide, a UV absorber, a coagulant and a biologically active peptide or protein.

* * * * *